United States Patent [19]

Feeny

[11] 4,162,913
[45] Jul. 31, 1979

[54] 1,2-DIMETHYL-3,5-DIPHENYLPYRAZOLI-UM-2,2-DICHLOROPROPIONATE

[75] Inventor: Richard W. Feeny, Hightstown, N.J.

[73] Assignee: American Cyanamid Co., Stamford, Conn.

[21] Appl. No.: 622,299

[22] Filed: Oct. 14, 1975

Related U.S. Application Data

[62] Division of Ser. No. 307,689, Nov. 17, 1972, abandoned.

[51] Int. Cl.$^2$ ..................... A01N 9/22; C07D 231/10
[52] U.S. Cl. ........................................... 71/92; 71/113
[58] Field of Search ................. 71/92; 260/310 D, 311

[56] References Cited

U.S. PATENT DOCUMENTS

| | | | |
|---|---|---|---|
| 2,807,530 | 9/1957 | Barrons | 71/113 |
| 2,823,227 | 2/1958 | Pumpelly | 71/113 |
| 2,889,663 | 6/1959 | Eaton et al. | 71/113 |
| 2,951,754 | 9/1960 | Bishop | 71/113 |
| 3,413,300 | 11/1968 | Haertl | 71/113 |
| 3,646,059 | 2/1972 | Brantley | 71/92 |
| 3,882,142 | 5/1975 | Walworth et al. | 71/92 |

OTHER PUBLICATIONS

Elguero et al., "Recherches das la serie etc.," (1969) Bull. Soc. Chim. Fr., pp. 1687–1698 (1969).

*Primary Examiner*—Glennon H. Hollrah
*Attorney, Agent, or Firm*—H. G. Jackson

[57] ABSTRACT

The invention is novel compositions containing a pyrazolium salt and a polyhalocarboxylic acid, an alkali metal or alkaline earth metal polyhalocarboxylate salt useful in the control of wild oats and other undesirable grass plants. The invention includes a herbicidal salt of the pyrazolium cation and the polyhalocarboxylate anion.

2 Claims, No Drawings

1,2-DIMETHYL-3,5-DIPHENYLPYRAZOLIUM-2,2-DICHLOROPROPIONATE

This is a division of application Ser. No. 307,689, filed Nov. 17, 1972 now abandoned.

CROSS REFERENCE TO RELATED APPLICATIONS

Herbicidal activity of some of the 1,2-dialkyl-3,5-diphenylpyrazolium salts useful in the compositions of this invention is reported in Klingsberg and Walworth U.S. Pat. No. 3,882,142.

BACKGROUND OF THE INVENTION

1. Field of the Invention

The invention pertains to chemicals for herbicidal use.

2. Description of the Prior Art

Although polyhalocarboxylic acids and the alkali metal, alkaline earth metal, primary, secondary and tertiary lower alkylamine and lower alkanolamine polyhalocarboxylate salts are used commercially for the control of undesirable grasses, their use in combination with a wild oat herbicide effective for the control of *Avena fatua, Avena sterilis,* or *Avena ludoviciana* is not suggested by the prior art. When acceptable known wild herbicides are used in combination with other herbicidal agents, problems are generally encountered. This is evidenced by the fact that the most widely accepted wild oat herbicides, 4-chloro-2-butynyl N-(3-chlorophenyl)carbamate (BARBAN) and the ethyl ester of N-benzoyl-N-(3,4-dichlorophenyl)alanine (SD-30053), are not effective in control of wild oats when used in combination with other herbicides. For example, J. D. Nalewaja, North Dakota State University, Fargo, N.D., reported in The Research Report of the North Central Weed Control Conference, 1971, pages 32–33, in a paper entitled "SD-30053 Plus Broadleaf Herbicides," that at one pound per acre SD-30053 alone applied at the four-leaf stage of wild oats gave 70% control of wild oats. However, when applied in admixture at the same one pound per acre rate for SD-30053 plus 6 or 12 ounces per acre of 2,4-D, wild oat control dropped to 29% and 25%, respectively. Similarly, addition of 2 and 4 ounces per acre of DICAMBA to SD-30053 and 4 or 8 ounces per acre of BROMOXYNIL to SD-30053 reduced wild oat control to 29%, 24%, 53% and 53%, respectively. DICAMBA is 2-methoxy-3,6-dichlorobenzoic acid; BROMOXYNIL is 3,5-dibromo-4-hydroxybenzonitrile and 2,4-D is 2,4-dichlorophenoxyacetic acid.

It is, therefore, surprising to find that the combination of 1,2-dialkyl-3,5-diphenylpyrazolium compound with polyhalocarboxylic acids or the alkali metal, alkaline earth metal, lower alkylamine or lower alkanolamine salts of polyhalocarboxylates which are generally used for control of undesirable grasses is compatible and selective for wild oats to other undesirable grasses.

SUMMARY OF THE INVENTION

The invention relates to novel compositions and methods for the control of wild oats and other undesirable grass plants, and involves applying to the foliage of the undesirable plant species a herbicidally effective amount of the novel composition comprising (1) a mixture containing a pyrazolium salt and a polyhalocarboxylic acid, or an alkali metal, alkaline earth metal, or primary, secondary or tertiary lower alkylamine or lower alkanolamine polyhalocarboxylate salt; (2) a salt of the pyrazolium cation and the polyhalocarboxylate anion; or (3) a mixture of both 1 and 2, above.

The pyrazolium salts utilized in the mixtures of this invention are compounds of the formula:

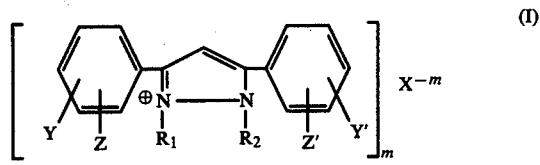

wherein $R_1$ is methyl; $R_2$ is alkyl $C_1$–$C_4$; Y, Y', Z and Z' each independently represent hydrogen, halogen, methyl or methoxy; X represents an anion having a charge of from 1 to 3; m represents an integer of 1, 2 or 3, and provided that only one phenyl ring in the above formula can be substituted on the carbon para to the pyrazolium ring with a substituent other than hydrogen.

The polyhalocarboxylate acids or salts used in the mixtures of the invention have the structure:

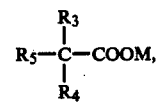

wherein $R_3$ and $R_4$ each represent halogen, preferably chloro or fluoro; $R_5$ represents halogen, methyl, halomethyl or dihalomethyl; and M represents an alkali metal ion, alkaline earth metal ion, hydrogen, or primary, secondary or tertiary lower alkylamine or lower alkanolamine cation. The term "lower" is intended to mean 1 to 4 carbon atoms.

In addition to the admixtures of the pyrazolium salt and the polyhalocarboxylate acid or salt, herbicidally active salts can also be formed consisting of the pyrazolium cation and the polyhalocarboxylate anion. These salts have the formula

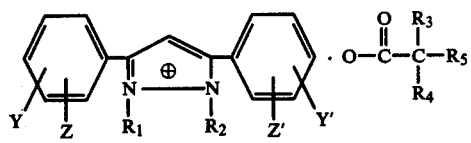

where $R_1$, $R_2$, $R_3$, $R_4$, $R_5$, Y, Y', Z and Z' are as described above. These salts are highly effective for the control of wild oats and other undesirable grass plants.

With regard to the pyrazolium compounds identified by structure I, above, suitable halogen substituents include fluoro, chloro, bromo and iodo. However, chloro, fluoro and bromo are preferred. Suitable anions include, for example, halides, such as chloride, bromide or iodide, acetate, sulfate, hydroxide, hydrogen sulfate, methyl sulfate, benzene sulfonate, $C_1$–$C_4$ alkoxy benzene sulfonate, $C_1$–$C_3$ alkyl benzene sulfonate, preferably toluenesulfonate, such as p-toluenesulfonate, nitrate phosphate, carbonate, hydrogen carbonate, $C_1$–$C_4$ alkane sulfonate, chlorate, perchlorate, thiocyanate, $Br_3^\ominus$, $I_3^\ominus$ and

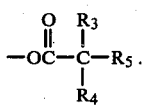

DESCRIPTION OF PREFERRED EMBODIMENTS

In practice, the pyrazolium-polyhalocarboxylate salt or the composition mixture of 1,2-dialkyl-3,5-pyrazolium salt, and the polyhalocarboxylic acid, alkali metal, alkaline earth metal, lower alkylamine or lower alkanolamine of the polyhalocarboxylate (preferably 2,2-dichloropropionic acid, sodium salt, trichloroacetic acid, sodium salt or 2,2,3,3-tetrafluoropropionic acid, sodium salt) is dissolved in water or a water/ketone or water/alcohol mixture and applied as a liquid spray to the foliage of undesirable plants. Usually about 0.1% to 5.0% by weight, and preferably 0.5% to 3.0% by weight, of a surfactant is added to the spray mixture to improve leaf and stem penetration. Among the types of surfactants which may be employed in these spray mixtures are the nonionic, anionic, cationic and nonionic-anionic surfactants. Nonionic surfactants are, however preferred, especially those having a hydrophylic-lipophylic balance between 11 and 16. Representative of the surfactants that can be used are the alkyl aryl polyglycol ethers, alkylphenol ethoxylates, trimethyl nonyl polyethylene glycol ether, nonylphenol ethylene oxide condensate, alkylphenol ethylene oxide condensate, stearaminopropyldimethyl-β-hydroxyethylammonium nitrate and di-coco-dimethylammonium chloride.

In practice, the pyrazolium salts and the polyhalocarboxylate acid or salts can also be individually prepared as wettable powders and mixed with water in the field in a spray tank. Again, it is desirable to provide about 0.1% to 5.0% of a surfactant in the aqueous mix. Similarly, each of the pyrazolium and polyhalocarboxylate compounds can be prepared as water dispersible concentrates. Where such concentrates are flowable liquids, they can be applied in low volume as the concentrate. Such concentrates may also be tank mixed in water and applied to the foliage of the undesirable plants as a dilute aqueous spray.

For effective control of undesirable plants, the herbicidal compositions of this invention are applied in sufficient amounts to provide from about 0.25 pound to 2.0 pounds per acre of the pyrazolium cation, and from about 0.14 pound to 8.0 pounds per acre of the polyhalocarboxylate compound, calculated as the acid.

Where the herbicidal composition is a mixture of the formula (I) pyrazolium salt and the polyhalocarboxylate acid or salt, it is generally most effective to apply said mixture to the foliage of the undesirable plants when the wild oats are at the two-leaf to early tillering stage and/or the grass plants are 2 inches to 16 inches in height. It is also generally preferable to apply a sufficient amount of the mixture to provide about 0.50 pound to 1.0 pound per acre of the pyrazolium cation, and about 2.0 pounds to 4.0 pounds per acre of the polyhalocarboxylate compound, calculated as the acid.

Where the herbicidal composition employed is the salt consisting of the pyrazolium cation and the polyhalocarboxylate anion, it will generally be found most effective to apply said composition when the wild oats are at the two-leaf to early tillering stage. It will also be found that effective control of wild oats and undesirable grasses is achieved when the salts are applied in sufficient amount to provide from about 0.25 pound to 2.0 pounds per acre of the pyrazolium cation and from about 0.14 pound to 1.15 pounds per acre of the polyhalocarboxylate anion.

Under certain conditions it may also be desirable to employ a mixture of the pyrazolium-polyhalocarboxylate salt and additional polyhalocarboxylic acid or salt. These mixtures are preferably applied at rates commensurate with those referred to above (i.e. 0.25 pound to 2.0 pounds per acre of pyrazolium cation and 0.14 pound to 8.0 pounds per acre of polyhalocarboxylate compound, calculated as the acid).

The compositions of this invention are useful for controlling wild oats and other undesirable grasses and can be used in the presence of potatoes, flax, peas, sugar beets, rape or sunflowers.

EXAMPLE 1

The following tests were conducted to demonstrate the compatability of 2,2-dichloropropionic acid, sodium salt with the pyrazolium salts for control of wild oats and other undesirable grasses. The grass species were grown in separate 2½ inch square plastic pots in the greenhouse. When the plants were two weeks of age, they were sprayed with an aqueous solution containing a sufficient amount of the pyrazolium cation to provide from about 0.50 pound to 1.0 pound per acre thereof, and from about 0.18 pound to 1.0 pound per acre of the 2,2-dichloropropionic acid. All test solutions were prepared in such a manner as to contain about 0.5% by weight of the biodegradable surfactant, polyoxyethylene sorbitan monolaurate. After the plants were treated with the test solutions, they were placed in the greenhouse and cared for commensurate with normal greenhouse procedures. Seventeen days after treatment, all plants were examined and rated for herbicidal activity using the rating system as previously described. In the rating system, 0 equals no effect and 9 equals complete kill. As can be seen in Table I, the pyrazolium compound employed alone had no effect on the annual grass species, barnyard grass(BA), crabgrass(CR) and green foxtail(GRF), but showed approximately 50% control of wild oats(WO) at the rates applied. It can also be seen that 2,2-dichloropropionic acid applied in the same manner provided good control of barnyard grass, crabgrass and green foxtail, but was less effective against wild oats than the pyrazolium compound. It can further be seen that when the pyrazolium compound and 2,2-dichloropropionic acid are combined, either as a mixture or as the salt, broad spectrum control of the undesirable grass species, barnyard grass, crabgrass, green foxtail and wild oats is achieved.

Results comparable to those in Table I are obtained when other compositions of the invention are used as herbicides.

TABLE I

| Structure | Treatment lb/Acre | Annual Grass Weeds | | | |
|---|---|---|---|---|---|
| | | BA | CR | GRF | WO |
| [1,2-dimethyl-3,5-diphenylpyrazolium · CH$_3$OSO$_2$—O$^\ominus$] | 0.5$^a$ | 0 | 0 | 0 | 5 |
| | 1.0$^a$ | 0 | 0 | 0 | 5 |
| CH$_3$CCl$_2$—COONa | 0.5$^b$ | 6 | 7 | 7 | 2 |
| | 1.0$^b$ | 8 | 8 | 7 | 5 |
| [pyrazolium · CH$_3$OSO$_2$—O$^\ominus$] + CH$_3$CCl$_2$—COONa | 0.5$^a$ + 0.5$^b$ | 3 | 7 | 6 | 6 |
| | 1.0$^a$ + 1.0$^b$ | 8 | 8 | 7 | 6 |
| [pyrazolium · CH$_3$CCl$_2$—COO$^-$] | 0.5$^a$ + 0.18$^b$ | 0 | 7 | 5 | 5 |
| | 1.0$^a$ + 0.36$^b$ | 7 | 7 | 6 | 5 |

$^a$Pounds per acre of pyrazolium cation.
$^b$Pounds per acre of dichloropropionic acid.

EXAMPLE 2

Preparation of 1,2-Dimethyl-3,5-diphenylpyrazolium 2,2-dichloropropionate

This example describes the preparation of the new compound of the invention 1,2-dimethyl-3,5-diphenylpyrazolium 2,2-dichloropropionate. 1,2-Dimethyl-3,5-diphenylpyrazolium hydroxide in an H$_2$O solution was titrated with 2,2-dichloropropionic acid (DALAPON) until pH 7 was obtained.

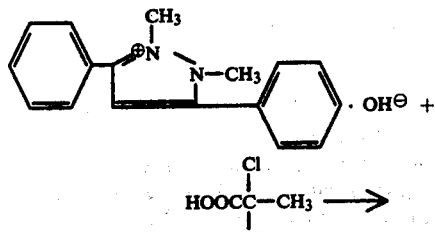

The H$_2$O solution was evaporated to an oil and azeotroped several times with toluene/acetone (dry). Hexane/acetone (approximately 5%) was added to the oil and it solidified to a light yellow solid, filtered, washed with hexane and dried to give 6.3 grams of product, melting point 141° C. to 143° C.

Analysis Calculated for N$_2$O$_2$Cl$_2$C$_{20}$H$_{20}$: C, 61.38; H, 5.15; N, 7.16. Found: C, 61.59; H, 5.17; N, 7.38.

EXAMPLE 3

Following the procedure of Example 1 above, effectiveness of 1,2-dimethyl-3,5-diphenylpyrazolium-2,2-dichloropropionate for controlling wild oats, barnyard grass, crabgrass and green foxtail is shown in Table II, below. The compositions are applied at the two-leaf stage of growth of the grasses and data obtained are reported below.

TABLE II

Grass in Two-Leaf Stage of Growth When Treated[1]

| Compound | lb./Acre | | Annual Weeds | | | | Crops | |
|---|---|---|---|---|---|---|---|---|
| | Cation | Anion | BA | CR | GRF | WO | WH* | BAR** |
| [diphenylpyrazolium · CH$_3$SO$_4^\ominus$] | 2.8 | 1.2 | 0 | 2 | 1 | 7 | 3 | 0 |
| | 0.7 | 0.3 | 0 | 1 | 1 | 7 | 3 | 0 |
| | 0.35 | 0.15 | 0 | 1 | 0 | 7 | 0 | 0 |

TABLE II-continued

| | Grass in Two-Leaf Stage of Growth When Treated[1] | | | | | | | |
|---|---|---|---|---|---|---|---|---|
| | lb./Acre | | Annual Weeds | | | | Crops | |
| Compound | Cation | Anion | BA | CR | GRF | WO | WH* | BAR** |
| [structure: 1,2-dimethyl-3,5-diphenylpyrazolium · CH₃C(Cl)₂—COO⁻] | 2.54 | + 1.46 | 9 | 9 | 9 | 9 | 8 | 6 |
| | 0.63 | + 0.36 | 7 | 7 | 7 | 7 | 6 | 0 |
| | 6.32 | + 0.18 | 3 | 6 | 7 | 7 | 5 | 0 |

*WH - Wheat
**BAR - Barley
[1]Herbicide Rating Scale:
0 = no effect
9 = complete kill The preparation of the formula (I) pyrazolium salts useful in the compositions of the invention is described below.

The pyrazolium salts (I) are conveniently prepared by first condensing the appropriate diketone with hydrazine or a $C_1$–$C_4$ lower alkyl hydrazine to form the corresponding 3,5-diphenylpyrazole. Thereafter, the pyrazole is alkylated to form the desired formula (I) pyrazolium salt.

Where hydrazine is employed in the condensation, alkylations are effected at the 1 and 2 positions. Where a lower alkyl hydrazine is employed in the initial condensation, alkylation is effected at the 2-position. These reactions are graphically depicted as follows:

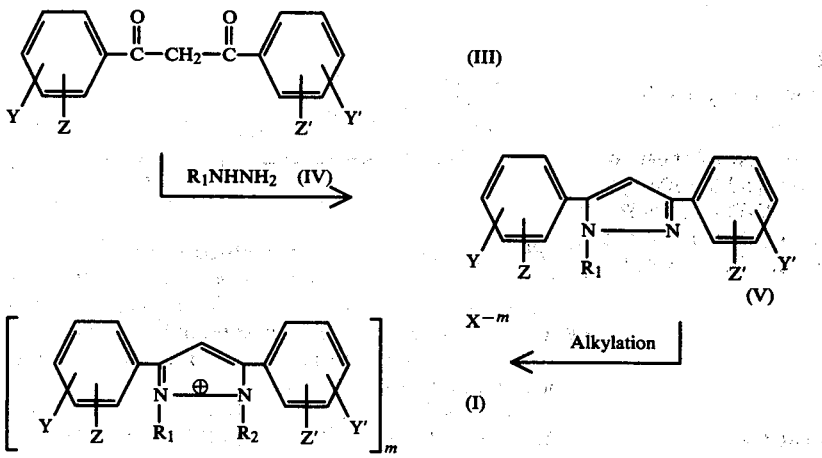

wherein m, $R_1$, $R_2$, Y, Y', Z, Z' and X are as described for formula I above; and R is hydrogen or lower alkyl of $C_1$–$C_4$.

Since the diketone and hydrazine compounds combine in equimolar quantities, it is preferable to maintain the molar ratio of reactants at about 1:1; however, a slight excess (up to about 10%) of either reactant may be used.

The ring-forming reaction between the hydrazine or alkyl hydrazine and the diketone is preferably carried out by combining the reactants in a solvent and heating to the reaction temperature. Suitable temperatures are in the range of from about 70° C. to about 150° C. and, preferably, between 80° C. and 120° C. Suitable solvents include, for example, aprotic solvents, such as, xylene, toluene, benzene, pyridine, DMSO, DMF, and the like, or protic solvents, such as, $C_1$–$C_4$ alcohols preferably, n- and iso-propanol. Where the latter solvents are employed, high rates of conversion are obtained at temperatures in the range of 80° C. to 85° C.

Where hydrazine is employed in the initial condensation reaction, alkylation of the resulting pyrazole is accomplished with conventional alkylating agents, preferably in the presence of an acid acceptor, such as, an alkali metal hydroxide or alkoxide, or a tertiary organic amine. Suitable bases include, for example, sodium methoxide, sodium hydroxide, triethylamine and the like.

The alkylation reactions are preferably conducted in the presence of a solvent, such as toluene, methylisobutylketone, n- or iso-propanol or an aqueous alcohol solution, such as a mixture of n-propanol and water.

Suitable alkylation reagents include, for example, alkyl halides, alkyl acetates, alkyl sulfates, alkyl nitrates, alkyl prosphates, alkyl carbonates, alkyl hydrogen sulfates, alkyl methyl sulfates and alkyl toluene sulfonates; wherein, said alkyl groups are in the range of from $C_1$–$C_4$ to provide the appropriate alkyl substituent in the formula (I) compound.

The pyrazole and alkylating reagent combine on an equimolar basis. However, it is often preferred to employ an excess of the alkylating agent. Optimum reaction conditions for effecting the alkylations will vary depending on the reactants employed. Reaction is effected by combining the alkylating agent, the pyrazole and, preferably, the acid acceptor and solvent. Reaction often occurs at room temperature. If not, the reaction mixture is heated until the reaction occurs. Where the alkylating reagents employed are volatile, such as, methyl chloride, the reaction is preferably conducted in a sealed vessel under pressure, to avoid loss of the reactants.

Quaternization of the 1-alkylpyrazole is effected by reaction thereof with at least an equimolar quantity of an alkylating agent, such as those mentioned above.

This reaction is preferably conducted in the presence of a solvent, such as, a lower alcohol $C_1$–$C_4$; a ketone, such as, acetone, methyl isobutyl ketone, methyl ethyl ketone or cyclohexanone; a chlorinated hydrocarbon, such as, chloroform; an ether, such as, diethyl ether, methyl ethyl ether or di-n-propyl ether; a molar aprotic solvent, such as, dimethyl sulfoxide or dimethylformamide; or, preferably, an aprotic solvent, such as, xylene, toluene or benzene.

The quaternization is effected by mixing the reactants and solvent at temperatures maintained between 35° C. and 150° C., preferably between 50° C. and 125° C.

Since the 1-alkylpyrazole and alkylating reagent combine in equimolar quantities, it is preferred to employ a 1:1 molar ratio thereof; however, an excess of either reagent may be employed.

As in the previously discussed alkylation reaction, where the alkylating agent is volatile at the temperatures used, such as in the case of methyl chloride, it is preferred to use a sealed pressure vessel to conduct the reaction.

Where the diketone selected is asymetrically substituted and $R_1$ differs from $R_2$ in the formula (I) compound to be produced, a mixture of isomers will result from the above synthetic scheme. In such cases, it is generally expedient to employ the isomer mixture in the herbicidal processes of the present invention. Where their separation is desired, however, it may be effected by conventional separation techniques, such as, for example, by fractional crystallization.

In carrying out the above ring closure and alkylation reactions, it may be expedient to initially form a salt having an anion other than that which it is desired to employ in the herbicidal processes of the present inventon. In such cases, the exchange in anion may be conveniently made in a subsequent step, such as that graphically depicted below:

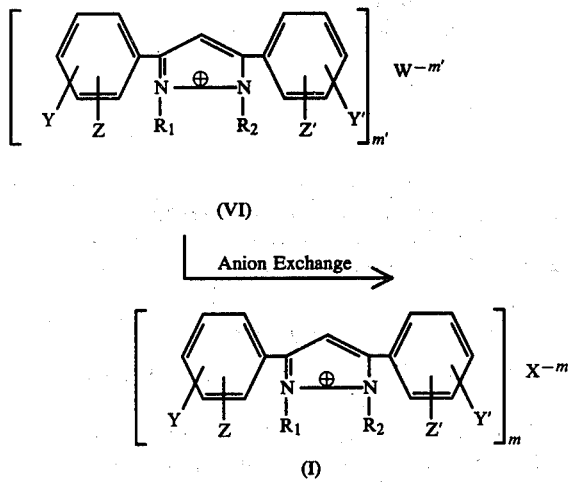

wherein m, $R_1$, $R_2$, Y, Y', Z and Z' are as defined for formula (I) above; m' is an integer selected from 1, 2, and 3; and W is an anion.

The exchange may be effected by treating the initially formed salt with an ion exchange resin. Among the suitable ion exchange resins, one may mention a strong base organic anion exchanger. Illustrative exchangers employ quaternary ammonium salts. Where the resin is supplied as the salt of an anion other than that desired, it is pretreated with an aqueous solution of a salt of the desired anion. For example, if the resin is supplied as a quaternary ammonium chloride and it is desired to produce a pyrazolium nitrate, one would pretreat the resin with an aqueous solution of sodium nitrate.

Other optional subsequent modifications of the anion in the pyrazolium salt may be effected. For example, a pyrazolium chloride may be conveniently converted to the corresponding bromide or iodide by treatment with NaBr or NaI, respectively, in a solvent, such as acetone. A pyrazolium salt, such as the chloride, may be converted to the corresponding perchlorate by treatment of an aqueous solution of said salt with perchloric acid. However, the pyrazolium perchlorates differ measurably from other pyrazolium salts in that they exhibit extremely poor water solubility and are substantially more difficult to formulate since there is about a 100- to 1000-fold difference in their solubilities as compared with the other salts. This results in the precipitation of the less soluble perchlorate salt. The bromides or iodides may be conveniently converted to the tribromides or triiodides by adding bromine or iodine to a solution of the mono-bromide or mono-iodide in a solvent, such as ethanol.

EXAMPLE 4

Preparation of 1-Methyl-3,5-diphenylpyrazole

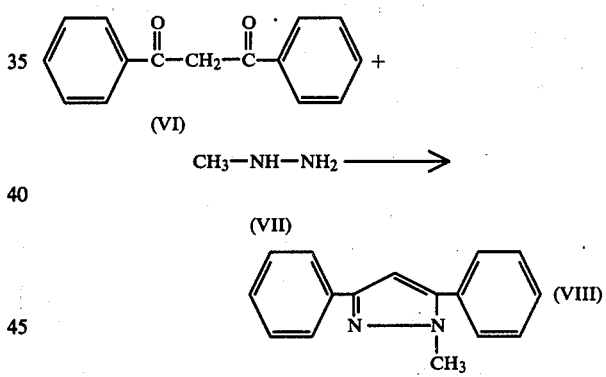

545.0 Grams (2.43 moles) of dibenzoylmethane and 533 ml. of pyridine are stirred together and heated to 80° C. 112 Grams (2.43 moles) of methylhydrazine are then slowly added to the mixture and a strong exothermic reaction ensues necessitating cooling of the mixture with a water bath. When addition is complete, the mixture is heated to reflux and maintained in this condition for 40 minutes. The mixture is then cooled to 30° C., poured into 19 liters of 3N HCl, filtered, and the solid collected. This is reslurried in 198 grams (2.43 moles) of sodium acetate dissolved in 19 liters of water. The mixture is filtered, water washed and air dried to give 535 grams of product, 94.5% yield, having melting point 58° C. to 59° C.

Following the above procedure and substituting ethylhydrazine, n-propylhydrazine, isopropylhydrazine, sec-butylnydrazine, n-butylhydrazine, or isobutylhydrazine for methylhydrazine in the above reaction yields respectively: 1-ethyl-3,5-diphenylpyrazole; 1-n-propyl-3,5-diphenylpyrazole; 1-isopropyl-3,5-diphenylpyrazole; 1-sec-butyl-3,5-diphenylpyrazole; 1-n-butyl-3,5-diphenylpyrazole; and 1-isobutyl-3,5-diphenylpyrazole.

EXAMPLE 6

Preparation of 1,2-Dimethyl-3,5-diphenylpyrazolium p-toluene sulfonate

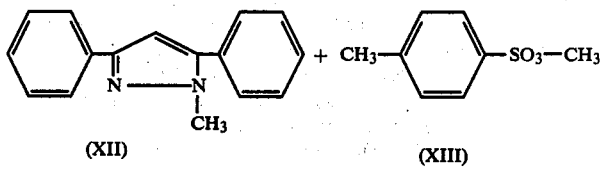

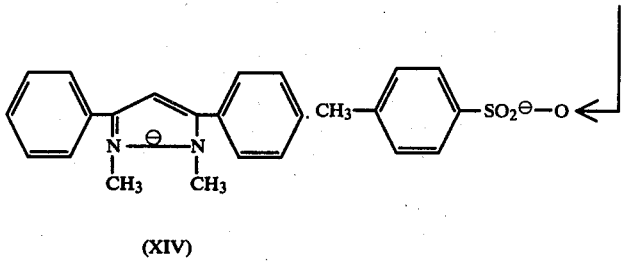

EXAMPLE 5

Reaction of the appropriately substituted dibenzoylmethane with the appropriate alkylhydrazine under the conditions of Example 4 results in the preparation of 1-alkyl-3,5-substituted diphenylpyrazoles. Graphically, the process may be illustrated as follows:

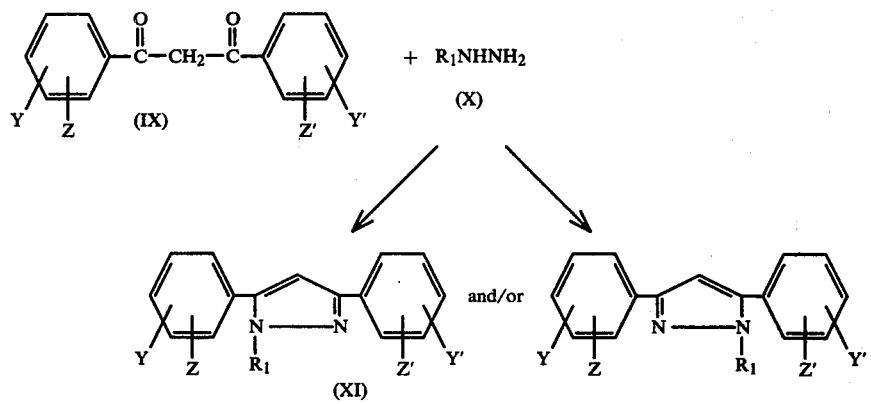

Among the compounds which can be prepared by this reaction are those identified in the Table below. For compounds in this Table, Y' and Z' are both hydrogen.

TABLE III

| Y | Z | $R_1$ | m.p. °C. |
|---|---|---|---|
| Cl (3) | H | $CH_3$ | |
| Cl (4) | H | $CH_3$ | 127.5–128.5 |
| Br (4) | H | $CH_3$ | |
| $CH_3$ (4) | H | $CH_3$ | 101.5–103 |
| $OCH_3$ (3) | H | $CH_3$ | |
| $OCH_3$ (4) | H | $CH_3$ | 105–106.5 |
| Cl (3) | Cl (4) | $CH_3$ | |
| Br (3) | Br (5) | $C_2H_5$ | |
| Br (3) | Cl (4) | $CH_3$ | |
| $CH_3$ (2) | $CH_3$(6) | $CH_3$ | |
| $OCH_3$(3) | $OCH_3$ (4) | $C_3H_7$-n | |
| Cl (4) | H | $C_4H_9$-sec | |
| Br (3) | H | $C_4H_9$-n | |
| $CH_3$ (4) | Cl (3) | $CH_3$ | |
| $CH_3$ (3) | $OCH_3$ (4) | $CH_3$ | |
| $OCH_3$ (4) | H | $C_4H_9$-sec | |

400 Grams (1.71 moles) of 1-methyl-3,5-diphenylpyrazole is dissolved in 2100 ml. of xylene and the solution thus prepared dried by azeotropic distillation. The solution is cooled to 70° C. and 318 grams (1.71 moles) of methyl-p-toluene sulfonate is added. The mixture is then refluxed for one hour and cooled causing the product to crystallize. When the mixture is cooled to 40° C., 1000 ml. of acetone are added. The mixture is filtered, washed with acetone, and dried in vacuo yielding 495 grams(69%) of product having a melting point of 177° C. to 178° C.

EXAMPLE 7

Preparation of 1,2-Dimethyl-3,5-diphenylpyrazolium iodide 5.0 Grams of 1-methyl-3,5-diphenylpyrazole is dissolved in 30 ml. of dry benzene with heating and constant stirring. 30.4 Grams of methyl iodide is added to the mixture, and the mixture heated to reflux. After refluxing for 12 hours, the mixture is cooled and filtered. The filtrate is again refluxed and as product forms, it is separated from the mixture by filtration. The total amount of solid recovered is 1.21 grams, 15% yield, having a melting point of 167° C. to 169° C.

EXAMPLE 8

Preparation of 1,2-Dimethyl-3,5-diphenylpyrazolium hydrogen sulfate and methyl sulfate 5.0 Grams of 1-methyl-3,5-diphenylpyrazole is dissolved in 30 ml. of dry xylene with heating and constant stirring. The solution is cooled to 60° C., and 2.78 grams of dimethyl sulfate is added in 10 ml. of xylene. The mixture is then heated to 100° C. for 6 hours and allowed to cool. After cooling, the mixture is filtered. The solid which is recovered is stirred with dry acetone and the mixture filtered. This yields 3.91 grams of the methyl sulfate, 50.7% yield, having a melting point of 146° C. to 148° C.

The filtrate is then evaporated to remove acetone and the remaining residue is collected. The residue weight of 1.23 grams, 16.6% yield, is the desired hydrogen sulfate having a melting point of 188° C. to 189.5° C.

EXAMPLE 9

Following the general procedures of Examples 6, 7 or 8, substituting the appropriately substituted 1-alkyl-3,5-substituted diphenylpyrazole for 1-methyl-3,5-diphenylpyrazole and the appropriate alkyl-p-toluene sulfonate, alkyl halide or alkyl sulfate for the methyl-p-toluene sulfonate, methyl iodide or dimethyl sulfate, yields the corresponding 1,2-dialkyl substituted 3,5-diphenylpyrazolium salt. The reaction is graphically illustrated below:

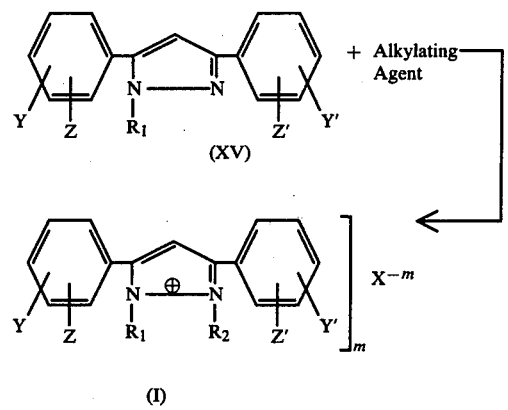

wherein $R_1$, $R_2$, X, Y, Y', Z, Z' and m are as described above for (I).

Among the compounds which can be prepared by this reaction are those identified in the table below, where Y' and Z' are both hydrogen.

TABLE IV

| | | | Reactants and Products | | | |
|---|---|---|---|---|---|---|
| Y | Z | $R_1$ | Alkylating Agent | $R_2$ | X | melting point °C. |
| Cl (3) | H | $CH_3$ | $CH_3$—⌬—$SO_2$—$OCH_3$ | $CH_3$ | $C_7H_7SO_3$ | |
| Br (4) | H | $CH_3$ | $CH_3$—⌬—$SO_2$—$OC_2H_5$ | $C_2H_5$ | $C_7H_7SO_3$ | |
| $CH_3$ (4) | H | $CH_3$ | $(CH_3)_2SO_4$ | $CH_3$ | $CH_3SO_4$ | 174–176 |
| $OCH_2$ (3) | H | $CH_3$ | $CH_3$—⌬—$SO_2$—$OCH_3$ | $CH_3$ | $C_7H_7SO_3$ | |
| Cl (3) | Cl (4) | $CH_3$ | $CH_2I$ | $CH_3$ | I | |
| Br (3) | Br (5) | $C_2H_5$ | $C_2H_5I$ | $C_2H_5$ | I | |
| $CH_2$ (2) | $CH_3$ (6) | $CH_3$ | n-$C_3H_7I$ | $C_3H_7$-n | I | |
| $OCH_2$ (3) | $OCH_3$ (4) | $C_3H_7$-n | i-$C_3H_7Br$ | $C_3H_7$-i | Br | |
| Cl (4) | H | $C_4H_9$-sec | $CH_3I$ | $CH_3$ | I | |
| Cl (4) | H | $C_4H_9$-sec | sec-$C_4H_9Br$ | $C_4H_9$-sec | Br | |
| $CH_3$ (4) | Cl (3) | $CH_3$ | $CH_3I$ | $CH_3$ | I | |
| $OCH_3$ (4) | H | $CH_3$ | $(CH_3)_2SO_4$ | $CH_3$ | $CH_3SO_4$ | 137–138.5 |
| $OCH_3$ (4) | H | $CH_3$ | $CH_3$—⌬—$SO_3CH_3$ | $CH_3$ | $C_7H_7SO_3$ | 127.5–129 |
| H | H | $CH_3$ | $(C_2H_5)_2SO_4$ | $C_2H_5$ | $C_2H_5SO_4$ | 109–111 |
| $CH_3$ (4) | H | $CH_3$ | $CH_3$—⌬—$SO_2OCH_3$ | $CH_3$ | $C_7H_7SO_2$ | 150–151.5 |

EXAMPLE 10

Preparation of 3,5-Diphenylpyrazole 22.4 Grams (0.10 moles) of dibenzoylmethane in 200 ml. of isopropyl alcohol are heated to reflux (approximately 85° C.), and to this is added hydrazine hydrate at a rate sufficient to maintain reflux. Thirty minutes after addition, the reaction is complete. The reaction mixture is permitted to cool and is then poured into water. The desired product as a fine white solid precipitates and is filtered, washed with cold water and dried, yielding 22.1 grams of product, melting point 198.5° C. to 200.5° C.

EXAMPLE 11

Preparation of 1-Methyl-3,5-diphenylpyrazole 5.0 Grams of dibenzoylmethane in 40 ml. of isopropanol is heated to 50° C. The temperature of the reaction mixture is then raised to about 85° C. and 10.5 grams of methyl hydrazine in 10 ml. of isopropanol added thereto. The mixture is heated at this temperature for 30 minutes, then cooled and cold water added thereto. A white solid precipitate forms and is filtered, washed and dried to yield 5.22 grams of product having a melting point of 59.5° C. to 60° C., 99+% yield.

EXAMPLE 12

Preparation of 1,2-Dimethyl-3,5-diphenylpyrazolium Perchlorate 4.7 Grams (0.02 moles) of 1-methyl-3,5-diphenylpyrazole is added to a solution of methyl chloride, 1.5 grams (0.03 moles) in 35 ml. of n-propanol maintained at −40° C. The mixture is then heated to 100° C. and evaporated to a bright green oil. On addition of hexane and cooling, the pyrazolium chloride as a green solid precipitates. The solid is washed with water and dissolved in 60 ml. of $H_2O$ and then $HClO_4$ added. The pyrazolium perchlorate as a white precipitate forms. It is filtered, washed with water and dried to yield the desired product.

EXAMPLE 13

Preparation of 1,2-Dimethyl-3,5-diphenylpyrazolium Methylsulfate

375 Grams (1.6 moles) of 1-methyl-3,5-diphenylpyrazole is dissolved in 1850 ml. of dry xylene and heated to 60° C. 208.13 Grams (1.65 moles) of dimethyl sulfate in 150 ml. of dry xylene is then added and the temperature of the reaction mixture raised to 105° C. to 110° C. and maintained there for 7.5 hours. The mixture is allowed to cool and then filtered. A brown solid is recovered, washed with xylene and then dry acetone to give the product in 88% yield, having a melting point of 155° C. to 157° C.

EXAMPLE 14

Preparation of 1,2-Dimethyl-3,5-diphenylpyrazolium bromide

A glass column is packed with a commercial grade of a trimethyl benzyl ammonium chloride, strong base organic anion exchange resin. The resin is washed thoroughly with an aqueous sodium bromide solution of 1 N concentration until $Br^-$ ion is detected in the eluent. Then an aqueous solution of 1,2-dimethyl-3,5-diphenylpyrazolium p-toluene sulfonate is passed down the column at a slow rate. The eluent is concentrated in vacuo, leaving the desired product as a residue after drying with a melting point of 188° C.-189° C.

Analysis: Calcd. for $C_{17}H_{17}N_2Br$: C, 62.01; H, 5.22; N, 8.54; Br, 24.22. Found: C, 61.98; H, 5.30; N, 8.54; Br, 24.27.

EXAMPLE 15

Following the general procedure of Example 14 above, substituting the appropriate sodium salt for the sodium bromide used therein and the appropriate pyrazolium p-toluene sulfonate for that used therein yields the compounds having the following formula and substituents set forth in the table below.

TABLE V

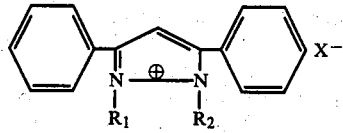

| Melting Point °C. | $R_1$ | $R_2$ | X |
|---|---|---|---|
| 100.5–103 | $CH_3$ | $CH_3$ | $OH . (3H_2O)$ |
| 56–58 | $CH_3$ | $CH_3$ | $\frac{1}{2} SO_4 . (2H_2O)$ |
| 140–141.5 | $CH_3$ | $CH_3$ | $NO_3$ |
| 188–189 | $CH_3$ | $CH_3$ | Br |
| 179.5–181 | $CH_3$ | $CH_3$ | $Cl . \frac{1}{2} H_2O$ |
| 168–169 | $CH_3$ | $CH_3$ | I |

EXAMPLE 16

Preparation of 1,2-Dimethyl-3,5-diphenylpyrazolium perchlorate

To a solution of 1,2-dimethyl-3,5-diphenylpyrazolium p-toluene sulfonate (10.0 g.) in 500 ml. of water is added a 20% aqueous solution of perchloric acid with vigorous stirring. The product separates immediately as a white solid. It is collected by filtration, washed with water and dried to give 8.3 g. of the desired product having a melting point of 183° C.-184° C., and the following elemental analysis:

Calcd. for $C_{17}H_{17}ClN_2O_4$: C, 58.75; H, 4.92; N, 8.05. Found: C, 58.21; H, 4.84; N, 7.95.

EXAMPLE 17

Following the general procedure of Example 16, substituting the appropriate pyrazolium p-toluene sulfonate for that used therein results in the formation of the perchlorates set forth in the table below.

TABLE VI

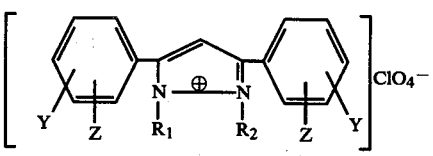

| | Substituents | | | |
|---|---|---|---|---|
| Y | Z | $R_1$ | $R_2$ | m.p. °C. |
| H | H | $CH_3$ | $-C_3H_7$-n | 145–146.5 |

EXAMPLE 18

Preparation of 1,2-Dimethyl-3,5-diphenylpyrazolium triiodide

To a solution of 2.0 grams (0.0053 moles) of 1,2-dimethyl-3,5-diphenylpyrazolium iodide in 100 ml. of aqueous ethanol (1:1) was adeed 1.34 grams (0.0053 moles) of iodine. The reaction mixture was allowed to sit with the resultant formation of a red precipitate.

The precipitate was collected by filtration, washed with aqueous ethanol and air dried to produce 3.0 grams of the desired triiodide having a melting point of 108°–110° C. and the following elemental analysis:

Calculated: C, 32.41%; H, 2.72%; N, 4.44%; I, 61.45%.

Found: C, 32.23%; H, 2.78%; N, 4.43%; I, 60.29%.

EXAMPLE 19

Following the general ring closing procedure of Example 4 and the alkylation procedure of Example 9, employing methylhydrazine and the appropriate diketones and alkylating agents yields the pyrazolium salts of the following formula, having the substituents set forth in the table below.

TABLE VII $$\left[ \begin{array}{c} \text{(pyrazolium structure with substituents Y, Z, } R_1, R_2, Z', Y'\text{)} \end{array} \right] X^{-m}_m$$

| X | Substituents | | | | | | Melting Point °C. |
|---|---|---|---|---|---|---|---|
|  | Y | Y' | Z | Z' | $R_1$ | $R_2$ |  |
| —OSO$_2$—C$_6$H$_4$—CH$_3$ | H | Cl (4) | H | H | CH$_3$ | CH$_3$ | 177.5–179 |
| —O—SO$_3$—CH$_3$ | H | Cl (4) | H | H | CH$_3$ | CH$_3$ | over 340 |
| —O—SO$_3$—CH$_3$ | H | Cl (4) | H | H | CH$_3$ | CH$_3$ | 217–219 |
| ClO$_4$ | H | Cl (4) | H | H | CH$_3$ | CH$_3$ | 136.5–138 |
| ClO$_4$ | H | H | H | H | CH$_3$ | C$_3$H$_7$-n | 145–146.5 |
| C$_2$H$_5$O—SO$_2$—O | H | H | H | H | CH$_3$ | C$_2$H$_5$ | 109–111 |
| CH$_3$O—SO$_2$—O | H | Cl (4) | H | H | CH$_3$ | CH$_3$ | 136.5–138 |
| CH$_3$O—SO$_2$—O | H | CH$_3$ (4) | H | H | CH$_3$ | CH$_3$ | 107–110 |
| ClO$_4$ | H | Cl (3) | H | H | CH$_3$ | CH$_3$ | 157–160 |
| ClO$_4$ | H | Cl (2) | H | H | CH$_3$ | CH$_3$ | 124–128 |
| CH$_3$O—SO$_2$—O | H | CH$_3$ (3) | H | H | CH$_3$ | CH$_3$ | 97–100 |
| ClO$_4$ | H | CH$_3$ (2) | H | H | CH$_3$ | CH$_3$ | 166–170 |
| ClO$_4$ | H | CH$_3$O (4) | H | H | CH$_3$ | CH$_3$ | 152–156 |
| CH$_3$O—SO$_2$—O | H | Cl (3) | H | Cl (5) | CH$_3$ | CH$_3$ | 162–164 |
| HSO$_4$ | H | Cl (2) | H | H | CH$_3$ | CH$_3$ | purple gum |
| CH$_3$O—SO$_2$—O | H | CH$_3$ (2) | H | H | CH$_3$ | CH$_3$ | brown gum |
| ClO$_4$ | Cl (3) | H | Cl (5) | H | CH$_3$ | CH$_3$ | 183–185 |
| CH$_3$O—SO$_2$—O | Cl (3) | H | Cl (4) | H | CH$_3$ | CH$_3$ | 152–153 |

I claim:

1. The compound 1,2-dimethyl-3,5-diphenylpyrazolium-2,2-dichloropropionate.

2. A method for the control of wild oats and other undesirable grasses comprising:
   applying to the foliage of the undesirable plant species a herbicidally effective amount of the compound 1,2-dimethyl-3,5-diphenylpyrazolium-2,2-dichloropropionate.

* * * * *